United States Patent [19]

Schachner et al.

[11] Patent Number: 4,889,112
[45] Date of Patent: Dec. 26, 1989

[54] APPARATUS FOR PERFORMING A TRACHEOSTOMY OPERATION

[75] Inventors: Aryeh Schachner, Givatayim; Yoel Ovil, Ramat Hasharon, both of Israel

[73] Assignee: Waltap Ltd., Surry Hills, Australia

[21] Appl. No.: 67,631

[22] Filed: Jun. 26, 1987

[30] Foreign Application Priority Data

Jan. 23, 1987 [IL] Israel .................................... 81378

[51] Int. Cl.$^4$ ...................... A61B 17/02; A61M 29/00
[52] U.S. Cl. ................................. 128/200.26; 128/17; 606/108; 606/185
[58] Field of Search ..................... 128/305.3, 321, 345, 128/322, 200.26, 343, 17

[56] References Cited

U.S. PATENT DOCUMENTS 2,629,568  9/1954  Wakefield .......................... 128/345
4,643,188  2/1987  Weiss ................................ 128/305.3

Primary Examiner—Michael H. Thaler
Attorney, Agent, or Firm—Christie, Parker & Hale

[57] ABSTRACT

Apparatus and method for performing a tracheostomy operation wherein the trachea is penetrated using a syringe needle (23) attached to a syringe (20) to form a small opening in the trachea. A guide wire (30) is inserted into the trachea through the needle (23) and after the syringe (20) is removed from the needle. The needle (23) is then removed from the trachea leaving the guide wire (30) inserted in the trachea. An instrument (T) specifically adapted for use in tracheostomy operations is inserted into the small trachea opening produced by the needle (23) while being guided by the guide wire (30). The instrument (T) being opened after insertion into the trachea to widen the trachea opening and a cannula for insertion into the opening of the trachea after having been widened by the instrument (T).

5 Claims, 5 Drawing Sheets

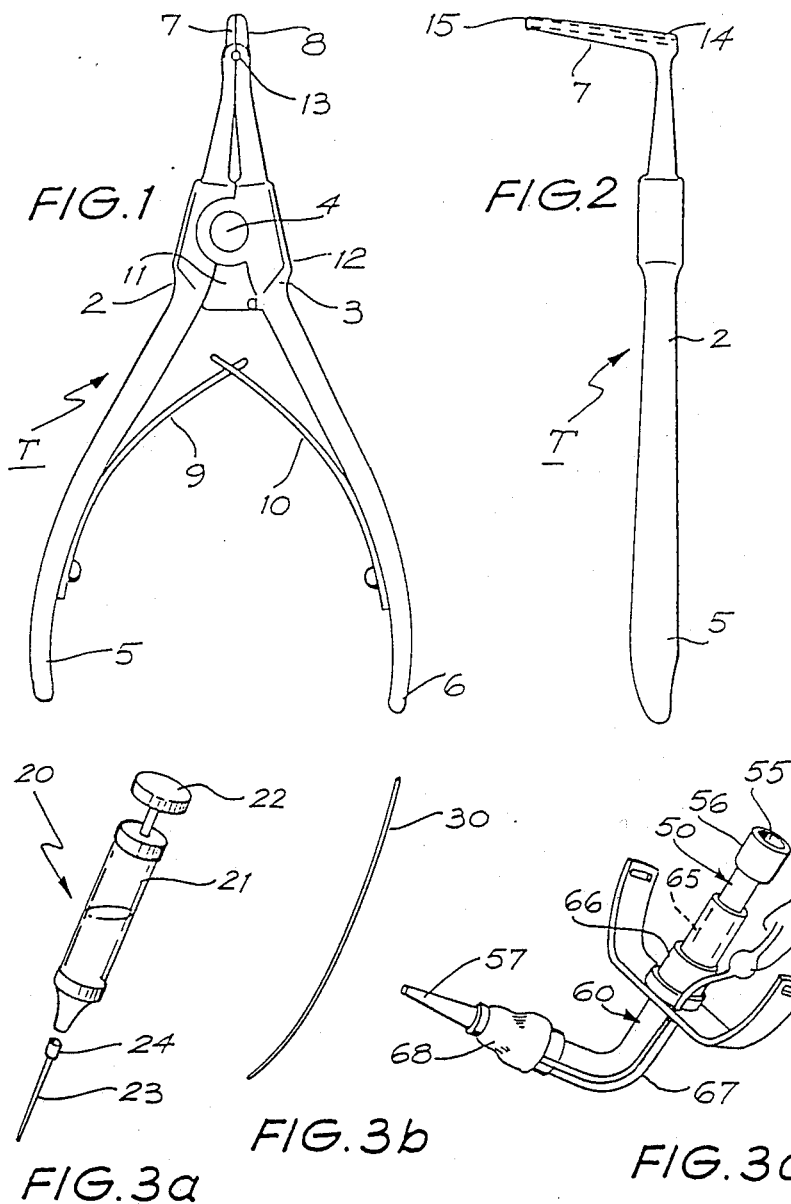

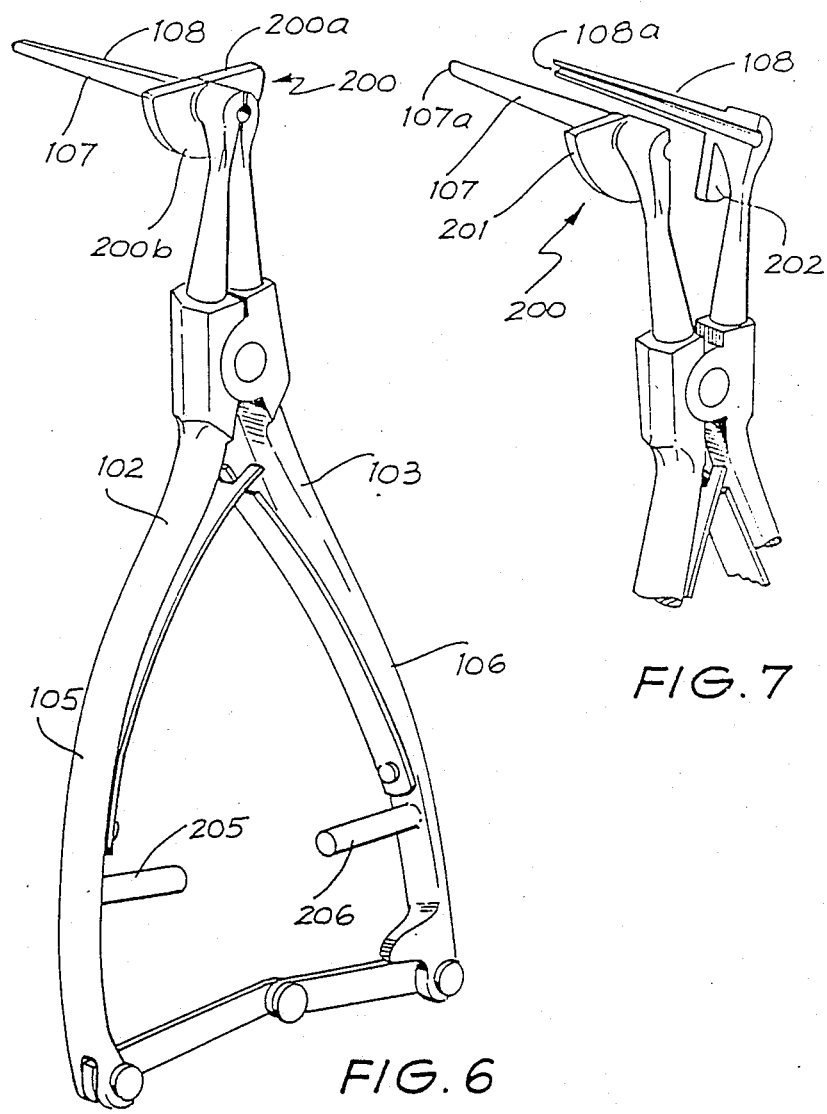

APPARATUS FOR PERFORMING A TRACHEOSTOMY OPERATION

The present invention relates to method and apparatus for inserting a cannula into a person's body. The invention is particularly applicable for performing a tracheostomy operation, and is therefore described below with respect to this application.

A tracheostomy is a surgical operation of cutting into the front of the trachea (windpipe) to relieve on obstruction and to maintain a clear airway. The operation involves opening the trachea and placing in the opening a cannula which provides the clear airway to the trachea. Although such an operation is frequently required as an emergency measure in order to prevent death by suffocation, the conventional procedure presently used is quite complicated and takes a considerable period of time, in the order of 30 minutes; moreover it is usually done only by a skilled surgeon since it is necessary to cut through blood vessels and to litigate them to the trachea because of the large size opening that is required.

An object of the present invention is to provide apparatus for use in performing a tracheostomy operation, and also to a method for performing such an operation, which apparatus and method have a number of advantages compared to the conventional procedure, as will be described more particularly below.

The invention is based on a method of performing a tracheostomy operation comprising the steps: penetrating the trachea to form a small opening therein by passing therethrough the needle of a syringe; manipulating the syringe to apply suction to the trachea; removing the syringe from the needle, with the needle remaining in the trachea; inserting a flexible guide wire via the needle into the trachea; removing the needle while retaining the guide wire in the trachea via the opening therein; widening the opening in the trachea; inserting a cannula into the opening; and removing the guide wire.

According to one aspect of the present invention, there is provided an instrument particularly useful in performing a tracheostomy operation on a subject, comprising: a pair of pivotable members pivotably mounted to each other at an intermediate location thereof; each of the pivotable members including a hand grip at one end and an elongated nose at the opposite end extending laterally of its respective pivotable member; the two elongated noses being formed at their inner confronting faces with comlementary recesses of slightly larger diameter than that of a wire inserted into an opening in the trachea of the subject; the outer faces of the two elongated noses being of substantially conical configuration decreasing in diameter towards their outer tips, facilitating the insertion of the noses into the trachea opening while guided by the wire therein; the two elongated noses being movable apart by squeezing the hand grips towards each other to widen the trachea opening and thereby to facilitate the insertion of a cannula therethrough.

According to another aspect of the invention there is provided apparatus particularly useful in performing a tracheostomy operation on a subject, comprising: a syringe and a syringe needle for penetrating the trachea by forming a small opening therein; a flexible guide wire insertable via the syringe needle into the trachea after the syringe has penetrated the trachea, and the syringe removed from the syringe needle; an instrument as described above for insertion into the small trachea opening when the instrument is in its closed position and while guided by the flexible guide wire, the instrument being manually opened to widen the trachea opening; and a cannula for insertion into the opening of the trachea after having been widened by the instrument.

The above method and apparatus for performing a tracheostomy operation provide a number of important advantages over the conventional procedure commonly used today: Thus, whereas the conventional procedure usually takes about 20–30 minutes, the novel procedure described above can be performed in a small fraction of this time, in the order of one minute or less; this makes the novel procedure particularly advantageous in emergency situations where there is a danger of death by suffocation. Further, the novel procedure does not require the expertise of a skilled surgeon, and may be performed by other doctors or paramedicals after relatively short instruction. In addition, the novel procedure is considerably safer since it can be performed quickly without litigation of blood vessels; and it involves less possibility of infection and less constriction of the trachea.

The novel procedure is particularly useful in emergency situations, but can also be used as an elective procedure at a hospital.

Further features and advantages of the invention will be apparent from the description below.

The invention is herein described, by way of example only, with reference to the accompanying drawings, wherein:

FIG. 1 illustrates one form of instrument particularly useful in performing a tracheostomy operation in accordance with the present invention;

FIG. 2 is a side view of the instrument of FIG. 1;

FIGS. 3a–3c illustrate the other components of the apparatus for use with the instrument of FIGS. 1 and 2 in performing a tracheostomy operation in accordance with the present invention;

Figure 5:
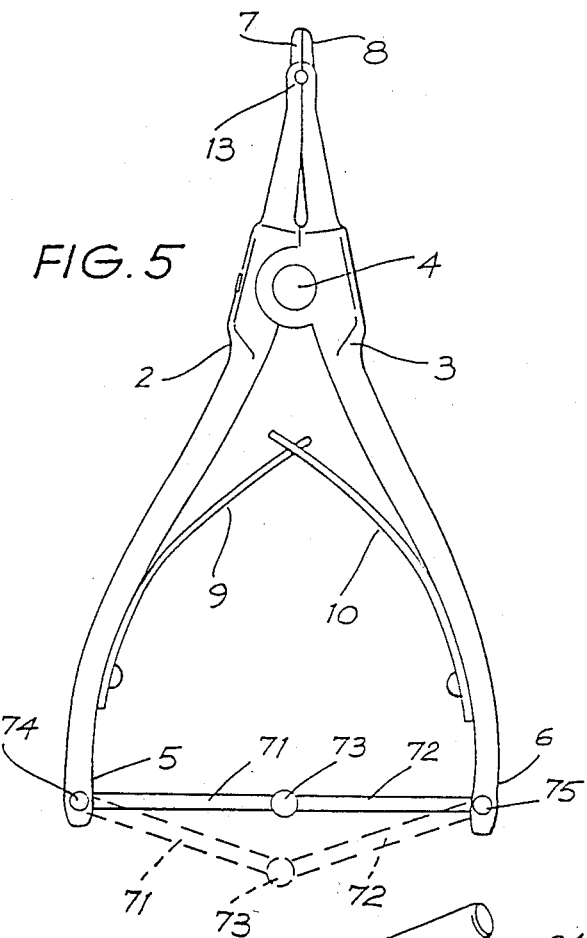
Figure 8:
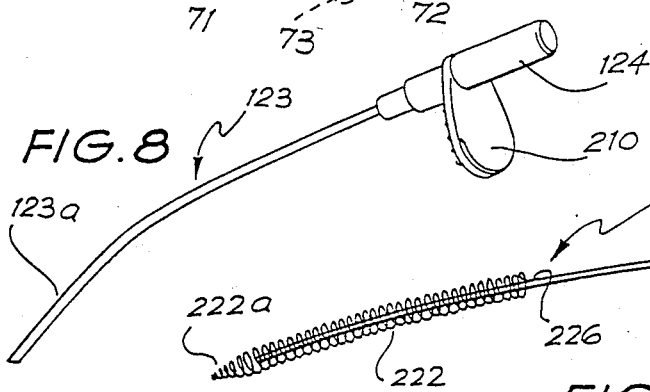
Figure 9:
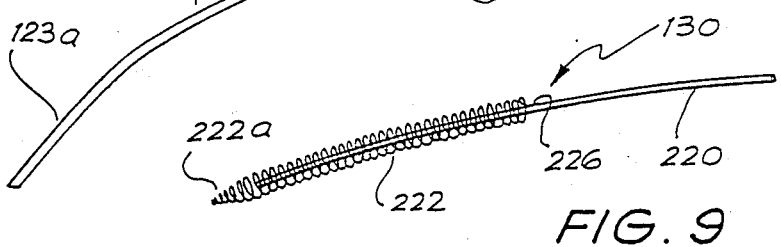

and FIGS. 4a–4j illustrate the steps in performing the tracheostomy operation in accordance with the present invention;

FIG. 5 illustrates a modification in the instrument of FIGS. 1 and 2;

FIG. 6 illustrates an improved dilator instrument;

FIG. 7 is a fragmentary view of the dilator instrument of FIG. 6 showing it in its open condition;

FIG. 8 illustrates an improved syringe needle;

FIG. 9 illustrates an improved flexible guide wire.

The instrument illustrated in FIGS. 1 and 2, and therein generally designated T, comprises a pair of pivotable members 2, 3, pivotably mounted at an intermediate location thereof about pine 4. Each of the two members includes a hand grip 5, 6 at one end of pivot 4, and an elongated nose 7, 8 at the opposite end. As shown particularly in FIG. 2, the two elongated noses 7, 8 extend laterally at an angle to their respective pivotable members 1, 2. The two pivotable members 1, 2 are urged to their closed positions as illustrated in FIG. 1 by a pair of springs 9, 10, and are locked in their closed positions by a locking member 11 pivotably mounted at 12 to member 6 just outwardly of pivot pin 4.

The two elongated noses 7, 8 are formed at their inner confronting faces with semi-cylindrical recesses 13 which complement each other to define a cylindrical recess for accomodating a wire (30, FIG. 3b) when the instrument is in the illustrated closed position. The outer faces of the two noses 7, 8 are of a tapered, conical configuration, decreasing uniformly in diameter from their junctures 14 with their respective pivotable members 5, 6, to their outer tips 15.

In addition to the instrument illustrated in FIGS. 1 and 2, the other elements used for performing a tracheostomy operation, include: a syringe, illustrated in FIG. 3a; a flexible wire illustrated in FIG. 3b, and a cannula having a mandrel, as illustrated in FIG. 3c. The procedure to be followed using these elements is described below with respect to FIGS. 4a–4j.

Syringe 20 (FIG. 3a) includes a liquid chamber 21, e.g. for saline water, a plunger 22, and a syringe needle 23 removably attachable to the syringe and having an enlarged annular shoulder 24 at the attachable end of the needle. Syringe 20 is used to form a small opening in the trachea by penetrating it via the syringe needle 23; and the liquid within chamber 21 of the syringe is used for providing an indication when the trachea has been completely penetrated by needle 23. Thus, as syringe needle 23 is applied to penetrate the trachea tube, plunger 22 is withdrawn outwardly to apply suction to chamber 21 so that as soon as the penetration is completed, air from the trachea is sucked into the liquid within chamber 21 and forms air bubbles in that chamber, which are easily discernible by the person performing the operation.

Wire 30 (FIG. 3b) is a flexible wire of small diameter, having an outer diameter smaller than the opening through syringe 23. The arrangement is such that after the syringe needle penetrates the trachea and the remainder of the syringe is removed from the needle, wire 30 may be inserted into the trachea via the passageway through the syringe needle. The syringe needle is then removed, and thereafter, wire 30 serves as a guide for guiding the application of the instrument illustrated in FIGS. 1 and 2 into the small opening in the trachea. The instrument is used for widening the opening sufficiently to receive mandrel 50 and cannula 60 as illustrated in FIG. 3c, which are inserted into the widened opening while guided by wire 30. The wire is then removed.

Mandrel 50 (FIG. 3c) includes a bore 55 extending its complete length, an enlarged head 56 at one end, and a tapered curved end 57 at its opposite end.

Cannula 60 (FIG. 3c), inserted with mandrel 50 into the widened opening in the trachea, is formed with a passageway therethrough for receiving mandrel 50, and with an enlarged head 66 connectable to a pumping device. The opposite end 67 of cannula 60 is curved, as shown, and receives a balloon 68 which may be inflated in order to plug the trachea and thereby to assure that the air pumped into it will pass into the subject's lungs and not through his mouth or nose. Cannula 66 is provided with a tubelet 69 leading to balloon 68 for inflating the balloon when the cannula is inserted into the trachea. Preferably, the outer end of tubelet 66 includes another small balloon 69' which also becomes inflated to provide an indication that balloon 68 within the trachea is inflated.

The enlarged head 24 of syringe needle 23, may also be connected to an air pump for pumping air into the trachea in an emergency situation.

FIGS. 4a–4j illustrate the steps involved in performing a tracheostomy operation in accordance with the apparatus shown in FIGS. 1–2 and 3a–3c.

Figure 4A:
Figure 4B:
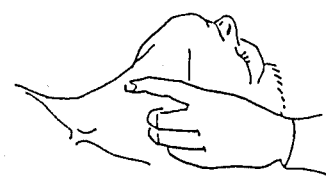

Thus, FIG. 4a illustrates the normal position of the subject before the procedure is started; and FIG. 2b illustrates the step of feeling the subject's throat in order to locate the trachea. This is not difficult to do because of the large size of the trachea.

Figure 4C:
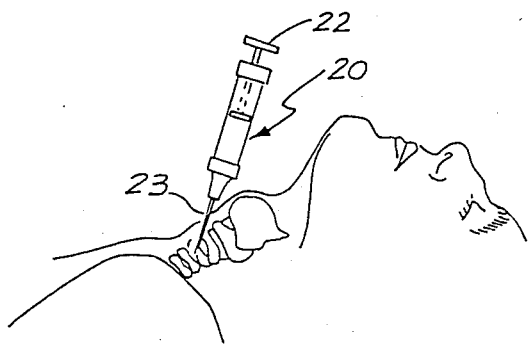
Figure 4D:
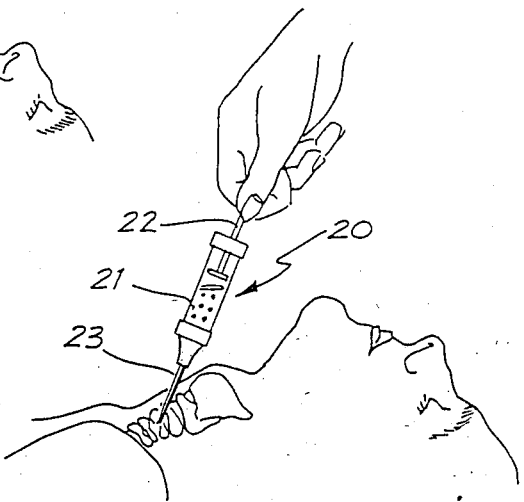
Figure 4E:
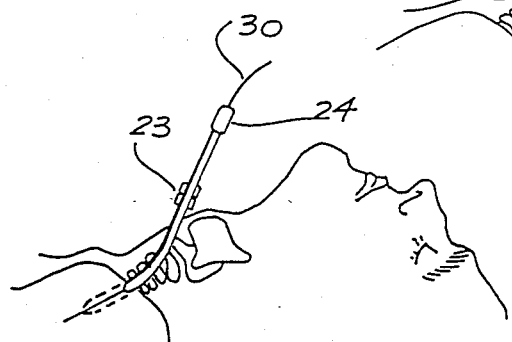
Figure 4F:
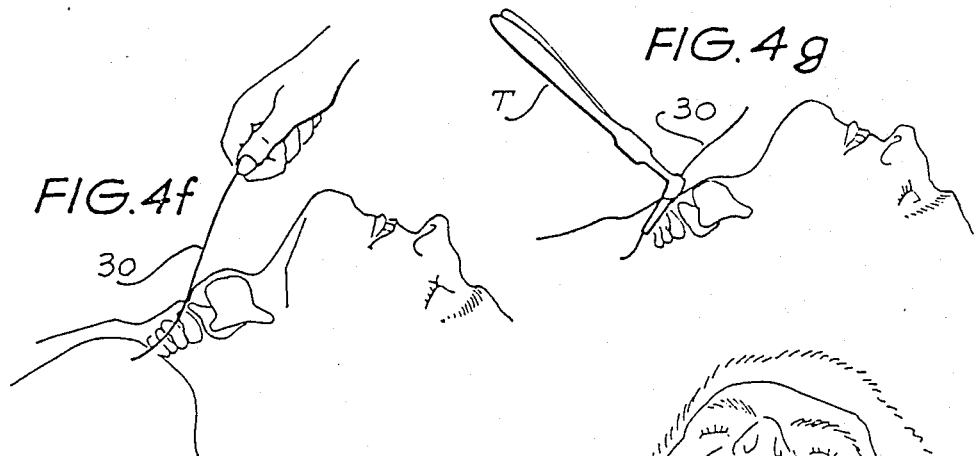
Figure 4G:
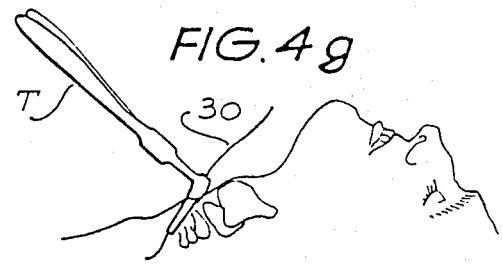
Figure 4H:
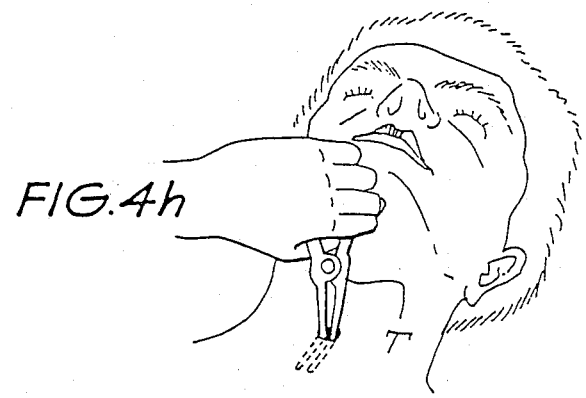
Figure 4I:
Figure 4J:
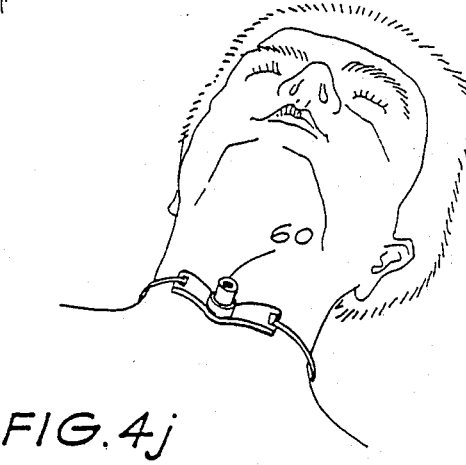

When the trachea has thus been located, syringe 20 is used to form a small opening in the trachea by passing the syringe needle 23 through it (FIG. 4c). During this procedure, plunger 22 is slightly withdrawn to apply a continuous suction to chamber 21 of the syringe, so that as soon as the syringe needle 23 has completely penetrated the wall of the trachea, air will be sucked into the liquid compartment 21 of the syringe and will be immediately discernable by the formation of bubbles within the liquid in that compartment, as illustrated in FIG. 4d. As soon as this occurs, syringe 20 is removed from the syringe needle, with the syringe needle remaining in the trachea. Guide wire 30 is then passed through the syringe needle into the trachea (FIG. 4e), and then the syringe needle is removed leaving the guide wire within the trachea (FIG. 4f).

The instrument illustrated in FIGS. 1 and 2 is then used for widening the small trachea opening. This is done by moving the instrument to its closed position as illustrated in FIG. 1 and locking it in that position by pivoting block 11 to the illustrated position wherein it prevents the two hand grips 5, 6 from being squeezed together to open the two noses 7, 8. While the two noses 7, 8 of the instrument are in the illustrated closed position, the outer end of the guide wire 30 is passed through opening 13 formed by the semi-cylindrical recesses in he confronting faces of the noses, so as to guide the noses into the small opening formed in the trachea tube (FIG. 4g); this is facilitated by the conical configuration of the outer surfaces of the two noses.

Block 11 is then pivoted to its unlocking position permitting the two hand grips 5, 6 to be squeezed toward each other, which causes the noses 7, 8 at the opposite ends to move away from each other (FIG. 4h), thereby widening the opening in the trachea.

When the trachea opening has been sufficiently widened, the wire 30 is removed, and the mandrel 50 and cannula 60 are inserted into the trachea opening (FIG. 4i) while the opening is held widened by the instrument. The mandrel 50 and guide wire 30 are then removed (FIG. 4j), leaving the cannula 60 alone in the trachea opening. The balloon 68 at the end of the cannula may then be inflated to block off the air passage from the trachea to the mouth and nose passageways of the subject, thereby to assure that the air through the cannula will pass into the subject's lungs, and will not escape through the mouth and nose passages of the subject. Proper inflation of balloon 68 is indicated by the inflation of small balloon 70 externally of the trachea.

As indicated earlier, if an emergency should arise during any of these operations and before the procedure has been completed, air may be pumped into the trachea via enlarged head 24 of syringe needle 23.

The function of mandrel 50 is to facilitate the introduction of cannula 60 into the trachea. The mandrel is thus inserted with the cannula into the trachea opening, and once the cannula is properly located within the opening, the mandrel is removed. If desired, mandrel 50 could be detachably coupled to cannula 60, as by the provision of a bayonet pin on the mandrel received within a bayone groove on the cannula, such that the cannula is coupled to the mandrel during the insertion of both into the trachea, and as soon as the cannula is properly located, the mandrel may be rotated slightly to unseat its pin from the cannula groove and then withdrawn while the cannula remains in place.

This procedure can be performed in 30-60 seconds, as compared to the 20-30 minutes required in the conventional tracheostomy procedure. The substantial time-saving makes it eminently suitable for emergency situations. Moreover, with relatively short instruction, the procedure can be performed by a doctor or paramedical and does not require the expertise of a skilled surgeon, thereby also making it particularly useful for emergency situations where a surgeon may not be availabe. Further, the described procedure does not involve cutting any arteries or veins and therefore is considerably safer to the patient, with less possibility of infection, than the conventional procedure.

Preferably, the noses 7, 8 of the instrument illustrated in FIGS. 1 and 2 are each of a length of 20-30 mm; extend at an angle of 90°-135° to their respective pivotable members; and their outer surfaces are of a diameter of 1-2.5 mm at their outer tips 15 increasing to a diameter of 3-5 mm at their junctures 14 with their respective pivotable members 2, 3. In the preferred embodiment illustrated in FIGS. 1 and 2, the noses are of a length of 25 mm, extend at an angle of about 100° to their respective pivotable members 2, 3; and their outer surfaces taper from an inner diameter of 2 mm to 4 mm. Their semi-cylindrical recesses 13 have a diameter slightly larger than the diameter of the flexible guide wire 30 which they receive; in the described preferred embodiment, flexible guide wire 30 has a diameter of 1.0 mm, and the recesses formed in the inner confronting faces of the noses 7, 8 have a diameter slightly larger, of about 1.5 mm.

FIG. 5 illustrates a modification in the construction of the instrument T of FIGS. 1 and 2. For the sake of comparison, the same reference numerals are used to identify the same parts.

It will be seen that in the modification of FIG. 5, the pivotable block 11 is omitted, and instead a pair of links 71, 72 are provided at the outer ends of the hand grips 5, 6 for locking them in the illustrated closed condition of the instrument. Thus, the two links 71, 72 are pivotably mounted to each other at their inner ends, as shown at 73, and are each pivotably mounted at their outer ends 74, 75 to their respective hand grips 5, 6. The arrangement is such that when the two links are in a straight line, as shown in full lines in FIG. 5, they lock the hand grips in their closed positions, but when the two links are non-aligned, which can be done by merely moving pivot 73 outwardly, the links unlock the handgrips and permit them to be pressed toward each other, to thereby spread apart the noses 7, 8, when widening the opening as described above.

An improved dilator instrument is illustrated in FIGS. 6 and 7. It is provided with a guard, generally designated 200, at the juncture of the pivotable members 102, 103 and their elongated noses 107, 108, to prevent undue penetration underneath the skin. Guard 200 is constituted of two sections 201, 202 are secured to the juncture of the respective pivotable member 102, 103 and its elongated nose 107, 108, so that it opens (FIG. 7) and closes (FIG. 6) with the elongated noses.

Each of the two guard sections 201, 202 is planar and of the general configuration of a quadrant of a circle, and each extends substantially parallel to its respective pivotable member 102, 103, such that when the pivotable members are in their closed positions (FIG. 6), the two guard sections together define a substantially semi-circular guard with the diametrical straight edge 200a substantially aligned with the elongated noses 107, 108, and with the curved edge 200b extending substantially below the elongated noses.

The elongated noses 107, 108 form an angle of 115° with their respective pivotable members 102, 103. In addition, each of the tips of the elongated noses is tapered, as shown at 107a, 108a, the taper preferably being 30°.

According to another improvement in the dilator instrument illustrated in FIGS. 6 and 7, the two handgrips 105, 106 are each provided with a stop member 205, 206 on their inner faces, such that the stops engage each other when the handgrips are squeezed, to limit the open position of the elongated noses 107, 108.

According to a further improvement, the syrine needle 23 includes a fingergrip holder 210 (FIG. 8) for holding it separately from the remainder of the syringe including the syringe compartment and the plunger. In addition, the syringe needle is slightly curved at its outer tip, as shown at 23a in FIG. 8. Such a construction has been found to facilitate the initial introduction of the syringe needle into the trachea by first inserting the syringe needle alone (i.e., without the remainder of the syringe) through the patient's skin into the trachea, and then applying the sryinge to the enlarged head 24 of the syringe needle, as will be described more particularly below.

According to a still further improvement, the metal guide wire 30, as shown in FIG. 9, includes an inner flexible core 220 and an outer flexible coil 222 thereover. One end of the outer coil 222 is secured, as by spot wedling or gluing at 226, to the inner wire core 220, and the outer tip of the coil projects past the inner core at the outer tip thereof to form a free conical tip 222a. Such an arrangement has been found to facilitate the introduction of the flexible guide wire via the syringe needle into the trachea.

The procedure for performing the tracheostomy operation is basically the same as described with respect to FIGS. 4a-4j, with the following modifications:

The patient should be lying on his back with the head extended, and the shoulders should be elevated (e.g., by using a rolled up sheet or blanket). The doctor pulpates the trachea to locate a spot about two centimeters above the supra-sternal notch.

The doctor, who should be positioned behind the patient, grasps the fingerpiece holder 210 of the syringe needle 23 and inserts the syringe needle into the trachea between the cartilage rings, this being facilitated by the curved tip of the needle. The syringe (not shown in the attached drawings) is then clamped to the syringe needle. In this case, the syringe compartment may be filled merely with air. The syringe plunger is pulled out to detect whether the piercing of the trachea has been completed, which is easily detected by the relatively free movement of the syringe plunger when this occurs. As soon as this has been detected, further penetration of the needle is discontinued; this insures that the front wall of the trachea is penetrated but not the rear wall. Then, the syringe is removed and the syringe needle 30 is retained in place in the trachea with the aid of the fingergrip holder 210.

The curvature of the syringe needle facilitates this manner of penetrating the trachea front wall without penetrating its rear wall.

After the syringe has been removed, the guide wire 30 is then inserted into the trachea via the hollow section of the syringe needle 23 until the guide wire extends completely into the trachea. This is facilitated by the outer coil 222 of the guide wire 30, and particularly by the conical end 222a of the coil projecting past the tip of the inner core wire 220. The needle is then removed, leaving the guide wire in place.

The dilator instrument illustrated in FIGS. 6 and 7 is then closed with the elongated noses 107, 108 around the guide wire, which guide wire is accomodated by the semi-cylindrical recesses formed in the noses; and the instrument is locked in its closed position by the locking links 171, 172, as illustrated in FIG. 6. The instrument is then advanced along the metal guide wire 30 until the tips of the noses enter the trachea. The locking links 171, 172 are then opened, and the handgrips 105, 106 are squeezed to spread apart the elongated noses 107, 108, and thereby to widen or dilate the opening through the trachea. This open position of the elongated noses 107, 108 is limited by the engagement of the stop elements 205, 206 carried by the handgrips 105, 106. The metal guide wire is then removed, and the cannula is introduced in the same manner as described above.

While the invention has been described with respect to one preferred embodiment, it will be appreciated that many other variations, modifications and applications of the invention may be made. For example, the described instrument and technique could also be used for introducing a cannula or other similar article into another part of a person's body.

What is claimed is:

1. An instrument particularly useful in performing a tracheostomy operation of a subject, comprising:
    a pair of pivotable members pivotably mounted to each other at an intermediate located thereof; each of said pivotable members including a hand grip at one end and an elongated nose at the opposite end extending 20-30 mm at an angle of 90°-135° laterally to its respective pivotable member;
    the two elongated noses being formed at their inner confronting faces with recesses;
    the outer faces of the two elongated noses being of substantially conical configuration decreasing in diameter towards their outer tips, facilitating the insertion of the noses into a trachea opening; said two elongated noses being movable apart by squeezing the hand grips towards each other to widen said trachea opening;
    a spring for urging the pair of pivotable members to their closed positions with the inner faces of their noses in abutting contact with each other, and a locking member comprising a pair of links pivotably mounted to each other at the inner ends and each pivotably mounted at its outer end to one of the hand grips for thereby locking the pair of pivotable members together in their closed position; said locking member being manually movable to unlock the pair of pivotable members and thereby to permit the hand grips to be squeezed together to move said noses apart; and
    a guard at the juncture of the pivotable members and their elongated noses, to prevent undue penetration underneath the skin;
    said guard including two sections, each section being secured to the juncture of one of the pivotable members and its respective elongated nose;
    wherein each of said guard sections is planar, of the general configuration of a quadrant of a circle, and extends substantially parallel to its respective pivotable member, such that when the pair of pivotable members are in their closed positions, the two guard sections together define a substantially semi-circular guard with the diametrical straight edge substantially aligned with the elongated noses, and with the curved edge below the elongated noses.

2. The instrument according to claim 1, wherein said recesses formed at the inner confronting faces of the two elongated noses are of a diameter of about 1.5 mm for accommodating a wire of about 1.0 mm diameter inserted into the opening in the trachea of the subject.

3. An instrument particularly useful in performing a tracheostomy operation of a subject, comprising:
    a pair of pivotable members pivotably mounted to each other at an intermediate located thereof; each of said pivotable members including a hand grip at one end and an elongated nose at the opposite end extending laterally to its respective pivotable member;
    the two elongated noses being formed at their inner confronting faces with recesses;
    the outer faces of the two elongated noses being of substantially conical configuration decreasing in diameter towards their outer tips, facilitating the insertion of the noses into a trachea opening; said two elongated noses being movable apart by squeezing the hand grips towards each other to widen said trachea opening; and
    a guard at the juncture of the pivotable members and their elongated noses, to prevent undue penetration underneath the skin;
    said guard including two sections, each section being secured to the juncture of one of the pivotable members and its respective elongated nose;
    wherein each of said guard sections is planar, of the general configuration of a quadrant of a circle, and extends substantially parallel to its respective pivotable member, such that when the pair of pivotable members are in their closed positions, the two guard sections together define a substantially semi-circular guard with the diametrical straight edge substantially aligned with the elongated noses, and with the curved edge below the elongated noses.

4. The instrument according to claim 3 wherein said recesses formed at the inner confronting faces of the two elongated noses are of a diameter of about 1.5 mm for accommodating a wire of about 1.0 mm diameter inserted into the opening in the trachea of the subject.

5. The instrument according to claim 3 in which said elongated nose at the opposite end extends 20-30 mm at an angle of 90°-135° laterally to its respective pivotable member.

* * * * *

UNITED STATES PATENT AND TRADEMARK OFFICE
CERTIFICATE OF CORRECTION

PATENT NO. : 4,889,112

DATED : December 26, 1989

INVENTOR(S) : A. Schachner; Y. Ovil

It is certified that error appears in the above-identified patent and that said Letters Patent is hereby corrected as shown below:

Column 1, line 58, change "towards" to -- toward --.

Column 2, line 18, change "paramedicals" to -- paramedics --.
Column 2, line 66, change "accomodating" to -- accommodating --.

Column 4, line 29, change "he" to -- the --.
Column 4, line 63, change "bayone" to -- bayonet --.

Column 5, line 6, change "paramedical" to -- paramedic --.
Column 5, line 9, change "availabe" to -- available --.
Column 5, lines 16, 17, change "privotable" to -- pivotable --.
Column 5, line 57, before "secured" delete "are" and insert --each--
Column 5, lines 58,59, change "member" to -- members --, "its" to -- their --, and "nose" to -- noses --.
Column 5, line 64, change "member" to -- members --.

Column 6, line 14, change "syrine" to -- syringe --.
Column 6, line 31, change "wedling" to -- welding --.

Column 7, line 7, change "accomodated" to -- accommodated --.

In the Claims:

Column 7, line 33, change "located" to -- location --.

UNITED STATES PATENT AND TRADEMARK OFFICE
CERTIFICATE OF CORRECTION

PATENT NO. : 4,889,112

DATED : December 26, 1989

INVENTOR(S) : A. Schachner; Y. Ovil

It is certified that error appears in the above-identified patent and that said Letters Patent is hereby corrected as shown below:

In the Claims

Column 7, line 54, change "position" to -- positions --.

Column 8, line 22, change "located" to -- location --.

Signed and Sealed this

Sixteenth Day of July, 1991

Attest:

HARRY F. MANBECK, JR.

Attesting Officer

Commissioner of Patents and Trademarks